United States Patent [19]

Sher

[11] Patent Number: 5,350,390
[45] Date of Patent: Sep. 27, 1994

[54] DEVICE FOR REMOVAL OF INTRALUMINAL OCCLUSIONS

[76] Inventor: Arieh Sher, 369 Congressional La., Rockville, Md. 20852

[21] Appl. No.: 83,760

[22] Filed: Jun. 30, 1993

Related U.S. Application Data

[63] Continuation of Ser. No. 857,556, Mar. 25, 1992, abandoned.

[51] Int. Cl.⁵ .............................................. A61B 17/32
[52] U.S. Cl. ................................... 606/159; 606/171; 606/180
[58] Field of Search ............... 606/159, 170, 171, 180; 604/22; 128/751, 755, 898; 15/104.05, 104.14, 104.15, 104.16

[56] References Cited

U.S. PATENT DOCUMENTS

| | | |
|---|---|---|
| 308,523 | 11/1884 | Sergeant . |
| 575,970 | 1/1897 | McCulloch . |
| 807,399 | 12/1905 | Rice, Jr. . |
| 1,173,326 | 2/1916 | Taylor et al. . |
| 1,623,411 | 4/1927 | Hulshizer . |
| 2,918,799 | 12/1959 | Geyer . |
| 3,766,952 | 10/1973 | Boers . |
| 3,911,793 | 10/1975 | Izumi . |
| 3,948,502 | 4/1976 | Waller et al. . |
| 3,961,559 | 6/1976 | Teramachi . |
| 4,036,309 | 7/1977 | Petreev et al. . |
| 4,092,213 | 5/1978 | Nishimura . |
| 4,114,517 | 9/1978 | Teramachi . |
| 4,265,434 | 5/1981 | Hamilton et al. . |
| 4,316,465 | 2/1982 | Dotson, Jr. . |
| 4,324,243 | 4/1982 | Helfgott et al. . |
| 4,484,510 | 11/1984 | Hirzel . |
| 4,508,327 | 4/1985 | Ersoy . |
| 4,631,052 | 12/1986 | Kensey . |
| 4,674,500 | 6/1987 | DeSatnick . |
| 4,749,376 | 6/1988 | Kensey et al. . |
| 4,770,174 | 9/1988 | Luckman et al. . |
| 4,784,636 | 11/1988 | Rydell . |
| 4,790,813 | 12/1988 | Kensey . |
| 4,819,635 | 4/1989 | Shapiro . |
| 4,850,957 | 7/1989 | Summers . |
| 4,957,482 | 9/1990 | Shiber . |
| 5,005,468 | 4/1991 | Ulle . |
| 5,024,651 | 6/1991 | Shiber . |
| 5,047,008 | 9/1991 | de Juan, Jr. et al. . |

FOREIGN PATENT DOCUMENTS

| | | |
|---|---|---|
| 29030 | 2/1916 | Fed. Rep. of Germany . |
| 2645009 | 10/1990 | France . |
| 0190105 | 11/1982 | Japan . |
| 8204293 | 12/1989 | PCT Int'l Appl. . |
| 8906517 | 10/1990 | PCT Int'l Appl. . |
| 222095 | 12/1968 | U.S.S.R. . |
| 568753 | 11/1977 | U.S.S.R. . |
| 717413 | 2/1980 | U.S.S.R. . |
| 929932 | 5/1982 | U.S.S.R. . |

*Primary Examiner*—Stephen C. Pellegrino
*Assistant Examiner*—William W. Lewis

[57] ABSTRACT

A method and device for removal of intraluminal occlusions which includes a catheter having a cutting head in a distal end thereof. The cutting head undergoes a simultaneous longitudinal and rotational movement by means of fluid pressure applied to a distal piston to which the cutting head is attached, The proximal end of the catheter includes a reciprocating pump which applies the fluid pressure to the distal piston. The cutting head is retractable to a sheathed or retracted position during insertion and movement in a patient. Material removed by the cutting head can either be collected in a chamber located between the distal piston and the cutting head or aspirated through the proximal end of the catheter.

24 Claims, 4 Drawing Sheets

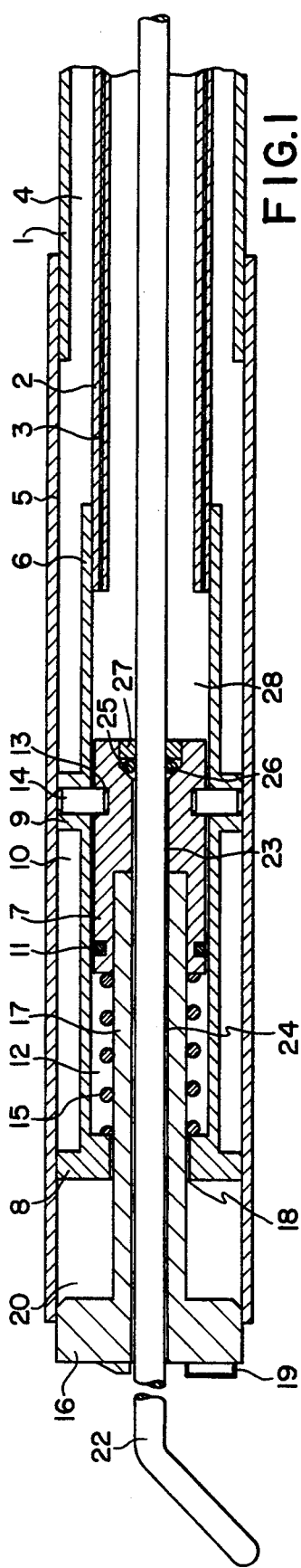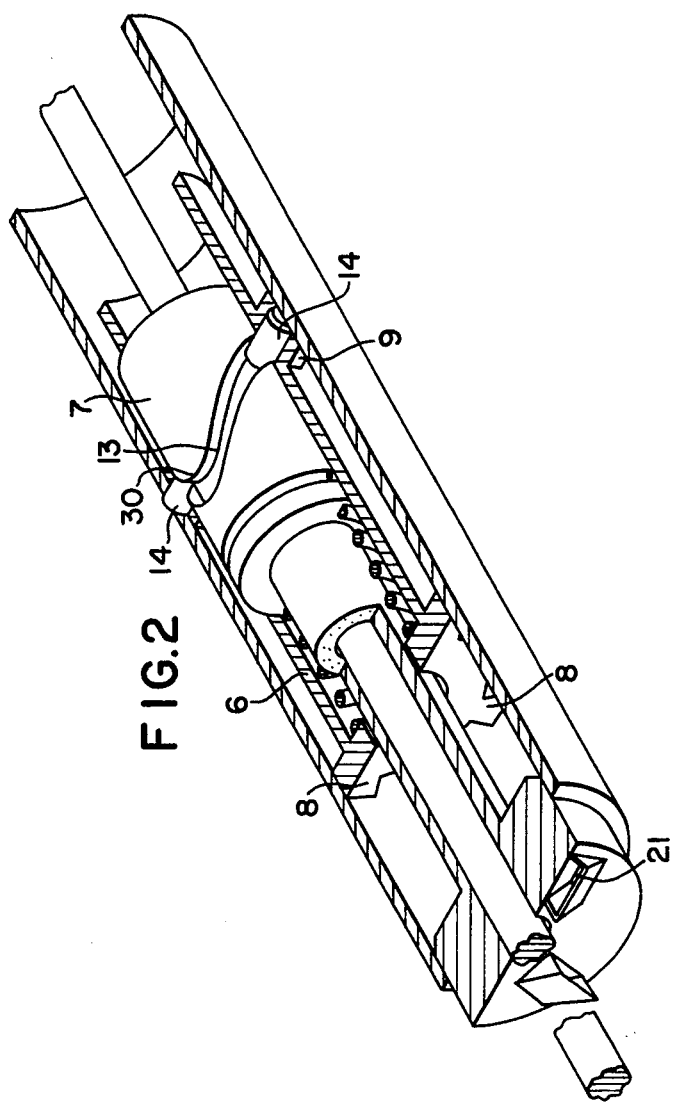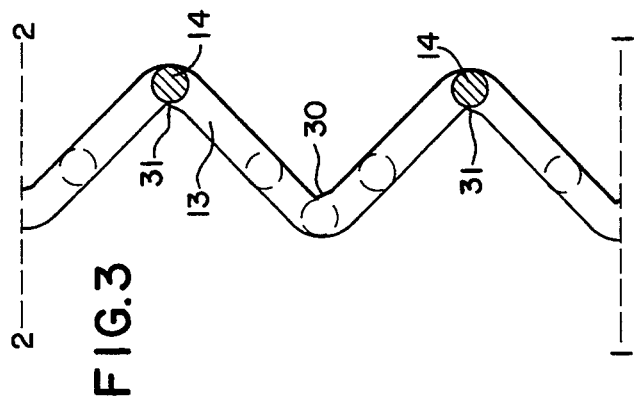

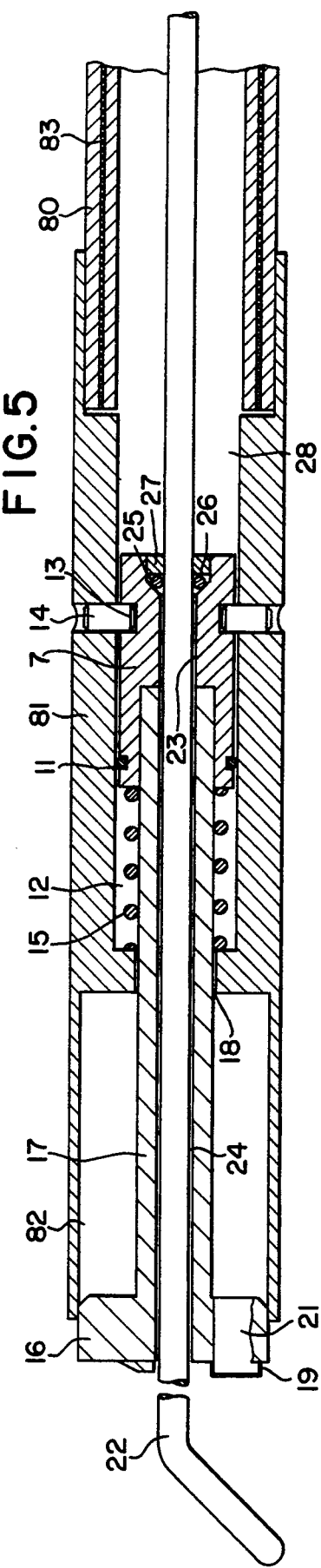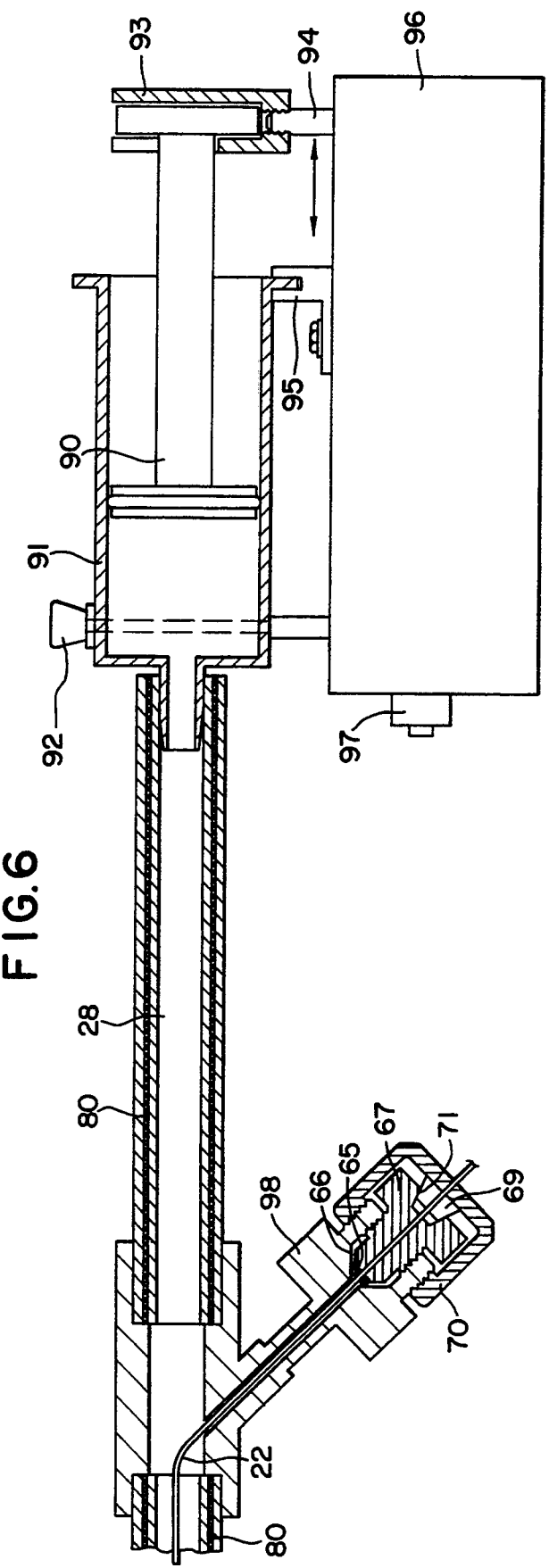

DEVICE FOR REMOVAL OF INTRALUMINAL OCCLUSIONS

CROSS REFERENCE TO RELATED APPLICATIONS

The present application is a continuation of U.S. patent application Ser. No. 07/857,556, filed on Mar. 25, 1992 now abandoned.

TECHNICAL FIELD

The present invention is directed to surgical instruments and procedures. More specifically, the present invention is directed to instruments and procedures for intravascular surgery and other surgical and in-body procedures.

BACKGROUND ART

Various types of devices have been suggested for removal of intraluminal occlusions. Generally, these devices may be classified according to the following aspects:
  (a) The manner by which occluding tissues are removed, e.g., the use of mechanical cutters, lasers, ultrasonic devices, fluid jets, etc.
  (b) The manner by which energy is transmitted to the cutting head, e.g., via flexible drive shafts, fluid power, electrical wires, etc.
  (c) The manner by which loosened tissue debris is removed, e.g., collecting the tissue debris in a collecting chamber next to the cutting head, aspirating the tissue fragments, fragmenting the tissue to very small particles, etc.

The following U.S. patents are believed to exemplify state-of-the-art surgical catheter devices.

U.S. Pat. No. 4,316,465 to Dotson discloses an ophthalmic cutter that comprises a driving device having a helical groove and helical ridges cooperating with the groove. A cutting device is connected to the driving device to sever any tissue which extends through an aspiration port of the aspiration needle.

U.S. Pat. No. 4,324,243 to Helfgott et al discloses an apparatus and process for aspirating and evacuating a pneumatically operated surgical instrument. A series of pneumatic pulses are generated and transmitted to a piston of a charging assembly and the surgical instrument to cause a hollow tube of the instrument to move toward the distal end of a cutting tube in a cutting stroke.

U.S. Pat. No. 4,674,500 to DeSatnick discloses the use of a protective sheath for a cutting blade. The blade remains in the sheath until ready for use.

U.S. Pat. No. 4,749,376 to Kensey et al discloses a reciprocating working head catheter. The catheter comprises a tubular body or jacket having a drive and a movable working head. The drive includes a drive wire that extends from the proximal end located outside the patient to the motion translation means. The cable is rotated at high speeds and the motion translation means converts the rotation of the drive cable to a rotating reciprocating motion of the working head.

U.S. Pat. No. 4,790,813 to Kensey discloses a catheter having a working head which is adapted to be rotated by a turbine drive while the head is advanced into a restriction in a passageway. The turbine includes structure to coaxially supply a drive fluid through a central passage to a rotatable cutting head or turbine head which includes turbine blades.

U.S. Pat. No. 4,819,635 to Shapiro discloses a tubular microsurgery cutting apparatus that includes an outer tubular member having an open end fixed to a housing of the driving end. An inner tubular sleeve has an open end and a cutting end that reciprocates within the tube. Reciprocation is produced by a piston which is driven by a source of pulsing air supplied through end cap through a tube.

U.S. Pat. No. 4,850,957 to Summers discloses an atherectomy catheter having an outer catheter tube and an inner catheter tube. A hydraulic motor is housed within the inner catheter tube and includes a cutting element connected to a drive shaft of the hydraulic motor. Fluid under pressure is forced into a stator cavity to provide power to turn or rotate a rotor.

U.S. Pat. No. 4,957,482 to Shiber discloses an atherectomy system for cutting, ingesting and removing obstructions from within an artery. A flexible catheter is disposed over a flexible guide wire which is insertable into an artery. A hollow blade having teeth is provided at the distal end of the catheter. The catheter is rotated by a motor coupled to the catheter through a hub and belt.

U.S. Pat. No. 5,024,651 to Shiber discloses an atherectomy system having a rotary flexible catheter for coring and ingesting obstructions. A flexible rotary catheter has coring means at its distal end. The catheter is slidably disposed in a sleeve. The sleeve has a window region near its distal end. The sleeve defines in the vessel a trajectory for the coring means to move along. Negative pressure for aspirating cut material can be applied through a rotary joint.

U.S. Pat. No. 5,047,008 to de Juan et al discloses a vitrectomy probe for removing vitreous materials having a blade which is located on the outer end of a tubular member which is attached to the end of a suction outlet tube. The blade is reciprocated by injecting pulsating pressurized fluid through a fluid inlet tube and port 22 into chamber 47. The pulses cause a diaphragm to push against a retainer connected to a suction outlet tube. The retainer and suction tube are urged away from the fluid chamber toward a stop ring causing a spring to be compressed and inner tubular member with blade to slide toward cutting position.

The present invention is directed to a catheter device for the removal of intraluminal occlusions which provides particular advantages over the prior art as discussed below.

DISCLOSURE OF THE INVENTION

It is one object of the present invention to provide a surgical device for removing intraluminal occlusions.

It is another object of the present invention to provide a catheter device for removing intraluminal occlusions.

Another object of the present invention is to provide a catheter device which includes a reciprocating and rotating cutting head.

It is a further object of the present invention to provide a catheter device which includes means to aspirate debris from a lumenal passage.

A further object of the present invention is to provide a catheter having a sheathable or retractable cutting head.

A still further object of the present invention is to provide a method of removing intraluminal occlusions.

A yet further object of the present invention is to provide a method of cutting and removing intraluminal occlusions with the use of a reciprocating and rotating cutting head.

According to these and further objects of the present invention which will become apparent as the description thereof is presented below, the present invention provides a device for removal of intraluminal occlusions which includes:

- a catheter having a distal end for insertion into a patient and a proximal end;
- a distal piston located within the distal end of the catheter for simultaneous longitudinal and rotational movement therein, the distal piston including a closed wave-shaped groove in a circumferential surface thereof which receives at least one stationary pin which is fixed to an inner portion of the distal end of the catheter and;
- a cutting head, the cutting head being attached to the distal piston for simultaneous longitudinal and rotational movement together with the distal piston.

The present invention further provides a method of removing intraluminal occlusions which involves:

providing a catheter having a distal end for insertion into a patient with a cutting head for simultaneous longitudinal and rotational movement;

inserting the distal end of the catheter into a lumen of a patient while maintaining the cutting head within the distal end of the catheter;

positioning the distal end of the catheter near an object to be removed and;

causing the cutting head to simultaneously move in both a longitudinal and a rotational movement so as to extend from the distal end of the catheter and cut the object to be removed.

BRIEF DESCRIPTION OF THE DRAWINGS

The present invention will be described with reference to the attached drawings which are given by way of non-limiting examples only. Wherever possible like reference numerals have been utilized to identify common elements throughout the figures.

FIG. 1 is a sectional view of the distal end of the apparatus according to one embodiment of the present invention.

FIG. 2 is an isometric view of the distal end of the embodiment of the invention of FIG. 1.

FIG. 3 is an illustration of the wave-shaped groove which shows the cutouts that determine the direction of the rotation of the distal piston.

FIG. 5 is a cross sectional view of an alternate embodiment of the distal end of the apparatus of the present invention.

FIG. 6 is a cross sectional view of an alternate embodiment of the proximal end of the apparatus of the present invention.

BEST MODE FOR CARRYING OUT THE INVENTION

Figure 4:
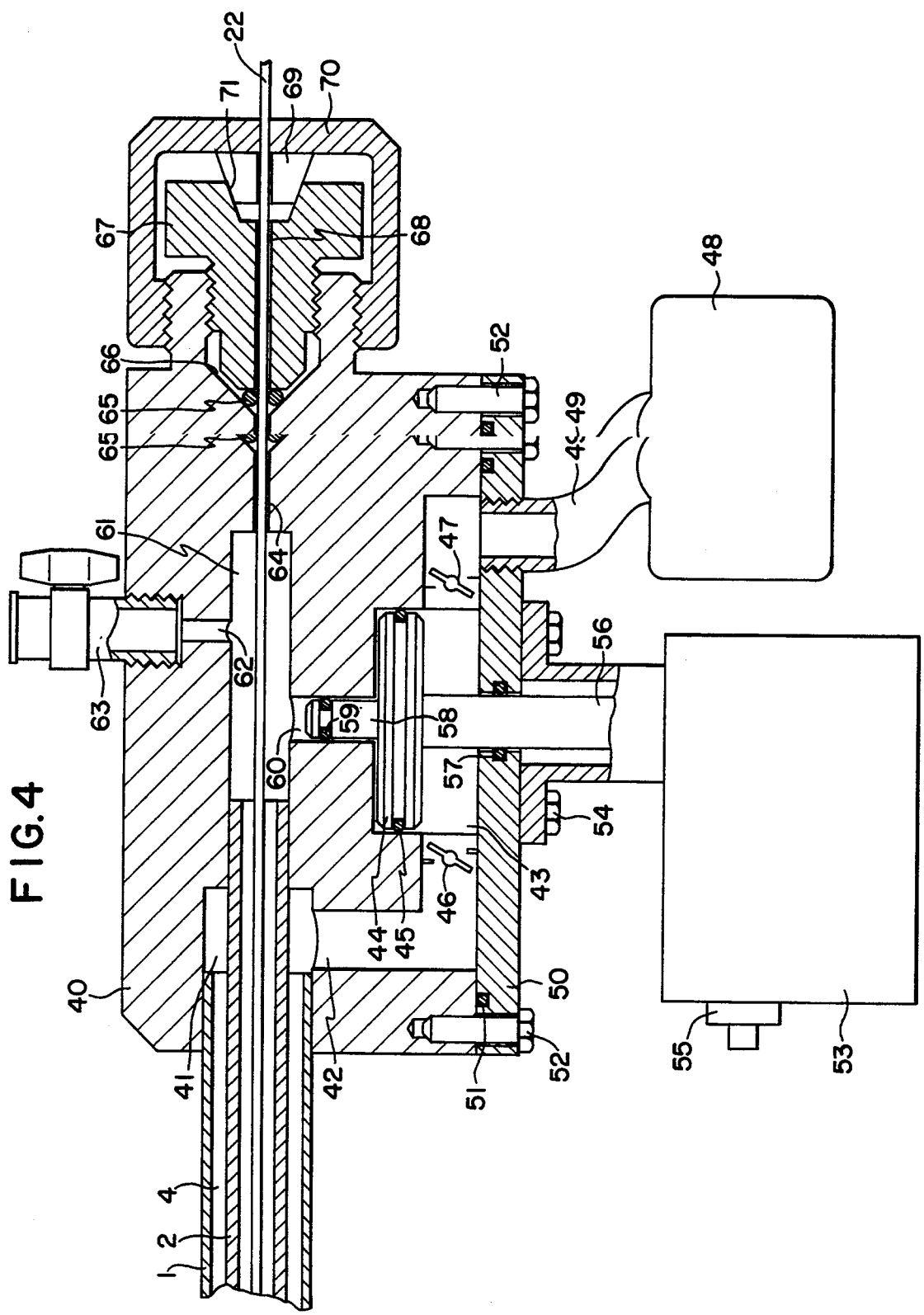
FIG. 4 is a cross sectional view of the proximal end of the apparatus according to one embodiment of the present invention.

Hereafter, the end of the catheter, which is designed to be inserted into the patient's body, shall be referred to as the "distal end". The other end, which is designed to remain outside a patient's body, shall be referred to as the "proximal end". In view of the above, "distal direction" or the term "distally" shall indicate a general direction from the proximal end to the distal end and "proximal direction" or "proximally" shall refer to an opposite direction.

The present invention provides for a catheter device which includes a cutting head for removing intraluminal occlusions. The cutting head is reciprocally movable from a first position in which it is sheathed by or retracted in the end of a catheter tube, to a second position in which the cutting head extends beyond the end of the catheter tube.

In addition to being reciprocally movable, the cutting head simultaneously rotates as it is moved reciprocally.

The simultaneous reciprocal and rotating movement of the cutting head is achieved by application of fluid, e.g., gas or liquid, pressure directly on a piston to which the cutting head is attached. Upon application of the fluid pressure, this piston simultaneously reciprocates and rotates. This movement of the piston is directly transferred to the cutting head which is attached to the piston.

As will be discussed below, the fluid pressure is pulsatile and the movement of the cutting head to the first or sheathed position is assisted by means of a spring biasing force.

Because the fluid acts directly on a piston (referred to below as the distal piston) to drive the cutting head and does not pass through the piston, only one tube is required to transmit the fluid pressure. This design is a particular advantage over prior devices which require multiple tubes to supply and remove fluid to turbines and other driving means.

The fluid pressure which acts on the distal piston is applied by another piston (to be referred to as the pressure piston) located at the proximal end of the catheter tube, which is connected to a reciprocating drive unit. The two above mentioned pistons move in unison. While pushing the pressure piston proximally, the pressure in the tube rises, resulting in movement of the distal piston in the same direction. Simultaneously, the distal piston undergoes a rotational movement as well, due to a wave-shaped groove located in its body, which is forced to rotate over stationary pins. As the pressure piston retracts proximally the pressure in the tube is reduced and the distal piston is forced to move proximally both by a spring force and by the vacuum created in the tube. Simultaneously, the distal piston and cutting head rotate in the same manner as explained above. This combined motion facilitates cutting of the occlusive material in the vessel.

The present invention provides means to remove tissue debris from the site at which the cutting head cuts an object, e.g., an occlusion. According to one embodiment of the present invention, removed debris is removed through an annular passage in the catheter. This annular passage is created when the above mentioned tube through which fluid pressure is applied to the distal piston is concentrically located inside another outer tube. In this embodiment it is possible to aspirate blood and cut material, e.g., tissue, debris by a third piston, (referred to below as the suction piston), located in the proximal end of the catheter device, or by a vacuum cylinder, or by an equivalent suction pump. According to another embodiment of the present invention, tissue debris is removed by collecting the debris in a collection chamber which is located between the cutting head and the distal piston.

As noted above, the cutting head can be positioned in a first sheathed or retracted position. When inserting and moving the distal end of the catheter in a patient, the cutting head is maintained in the first sheathed or retracted position in order to ensure safe passage and prevention of vessel perforation.

FIGS. 1–3 depict the distal end of the catheter according to one embodiment of the present invention. As shown in FIGS. 1 and 2 the catheter comprises an outer flexible tube 1. Concentrically positioned within outer tube 1 is an inner tube 2 which, if desired, can be provided with a braided reinforcement 3.

An annular passage 4 is defined between outer tube 1 and inner tube 2. The distal end of outer tube 1 is located in a jacket 5. A cylinder 6 is concentrically located in jacket 5. Cylinder 6 contacts jacket 5 only by a plurality of protrusions 8 at its distal end and a plurality of protrusions 9 at its proximal end. The plurality of protrusions 8 and 9 are discrete and are spaced evenly around the outer circumference of cylinder 6. Because spacings are provided between adjacent protrusions, an open annular passage 10 is defined between cylinder 6 and jacket 5. As discussed below, passage 10 enables removal of blood and tissue debris.

Inner tube 2 is connected at its distal end to cylinder 6. A distal piston 7 is housed within cylinder 6. Distal piston 7 is driven by fluid 28 applied through inner tube 2. A sealing means (e.g., O-ring) 11 at the distal end of distal piston 7 provides fluid-tight seal between the inner tube 2 and chamber 12. The pressure of fluid 28, which originates at the proximal end of the apparatus, fluctuates. The manner in which the pressure fluctuates will be discussed below with reference to FIG. 4.

As the pressure of fluid 28 rises in inner tube 2 distal piston 7 is forced distally in a rotational movement. The rotational movement of distal piston 7 is effected by the presence of a closed wave-shaped groove 13 formed in the outer circumferential surface of distal piston 7. The movement of distal piston 7 is directed by one or more stationary pins 14, which are assembled in cylinder 6 and protrude into wave-shaped groove 13. The pattern of closed wave-shape groove 13 may vary according to the number of pins 14, and according to the desired ratio of reciprocating to rotational movement.

Following a reduction in the fluid pressure in inner tube 2, distal piston 7 is pushed proximally by spring means 15 and drawn by a vacuum created in inner tube 2. Simultaneously, piston 7 undergoes a rotational movement in the same way as previously described; that is, by the cooperating action of the wave-shaped groove 13 and stationary pins 14.

A cutting head 16 is housed within jacket 5. The cutting head 16 has a stem 17 which passes through a central hole 18 in cylinder 6 and is connected to distal piston 7. The distal section of cutting head 16 has one or more cutting blades 19. Blood and tissue debris which are removed by the cutting head are drained to chamber 20 via openings 21 in cutting head 16 (FIG. 2). Because the cutting head 16 is connected to distal piston 7, it follows the same rotational and reciprocating motion as distal piston 7. This combined movement facilitates the incision of an occlusion.

In FIGS. 1 and 2 the cutting head 16 is shown at its most distal location. When no fluid pressure is applied to distal piston 7 through inner tube 2, spring 15 forces cutting head 16 to move proximally so that it is concealed in jacket 5. This manner of concealing the cutting head 16 ensures that no injury will be caused to lumenal walls during insertion of the catheter into a patient's vessel. The manner in which piston 7 rotates in a predetermined direction is explained with reference to FIG. 3 below.

Figure 7:
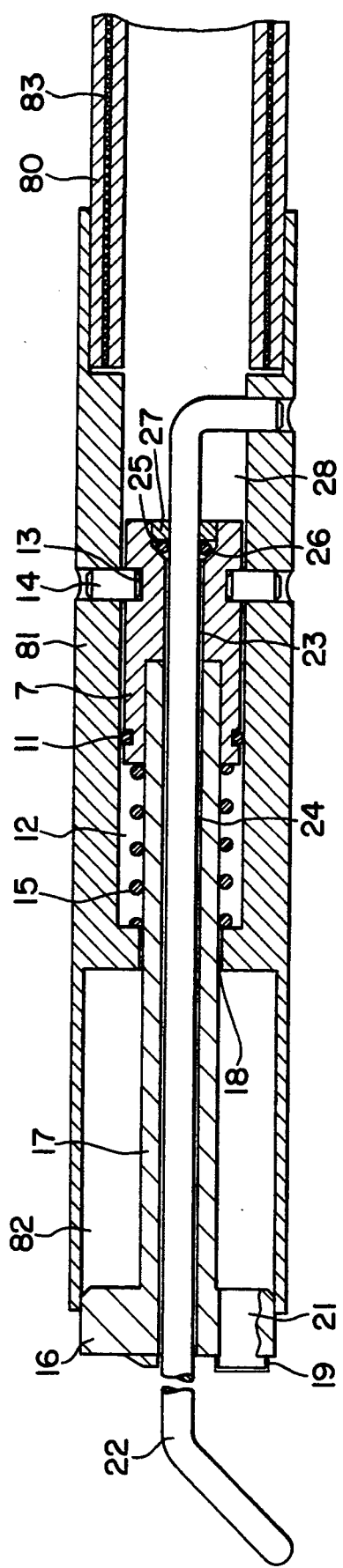
FIG. 7 is a sectional view of an alternative embodiment of the distal end of the apparatus in which the guide wire is of the fixed wire system type.
Figure 4:
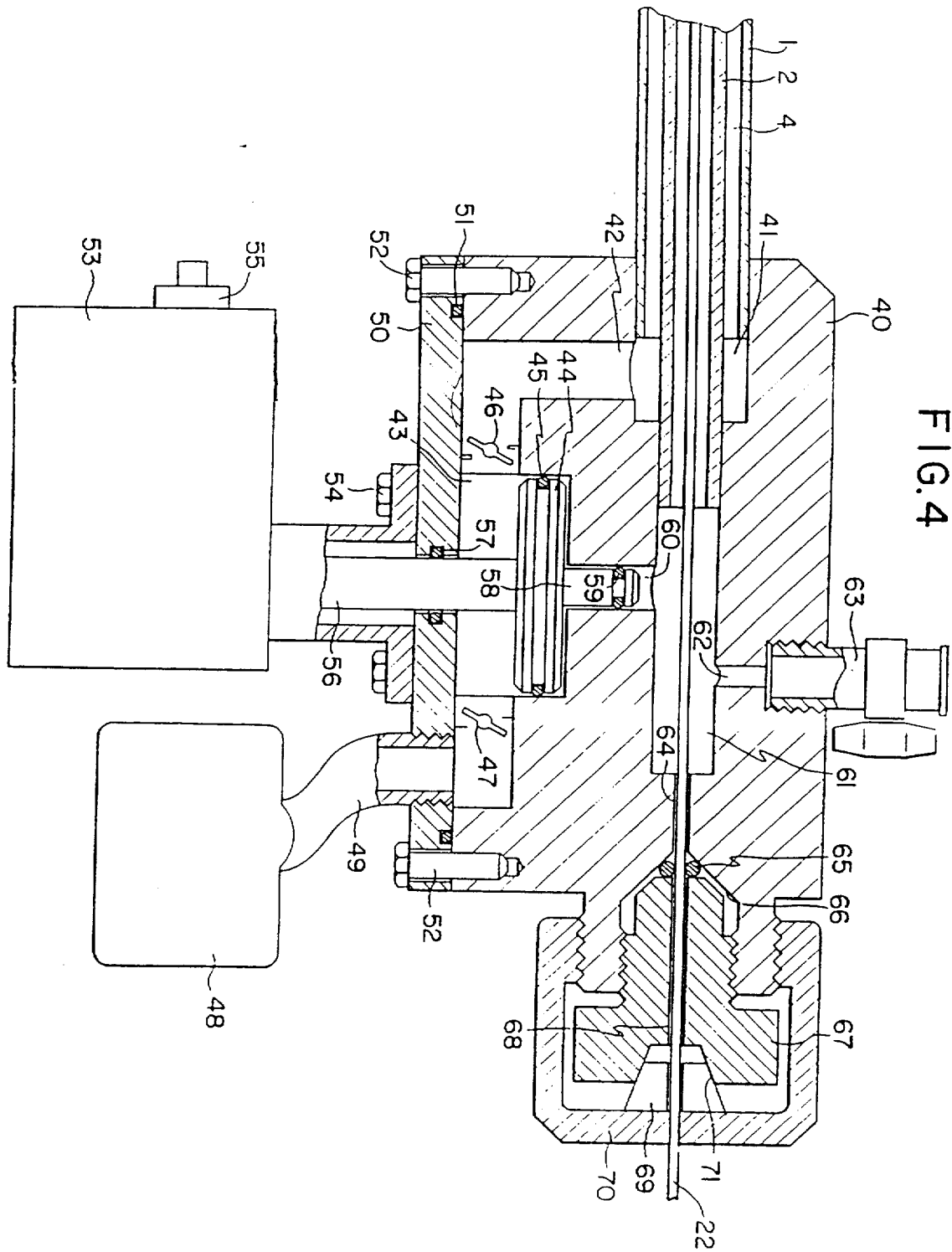

A guide wire 22 extends distally in front of cutting head 16 for guiding the catheter through a patient's vessel. Guide wire 22 passes through inner tube 2 all the way up to the proximal end. At the distal end guide wire 22 passes through hole 23 in distal piston 7 and through hole 24 in stem 17. According to another embodiment, guide wire 22 can be shorter and its proximal end can be connected to the inner circumference of cylinder 6. The guide wire, as shown in FIGS. 1 and 5, can extend through the catheter device. Alternatively, the guide wire can be of the fixed wire system type as shown in FIG. 7 in which one end of the guide wire 22 is fixed to the housing 81 of the catheter device.

A sealing means is provided for forming a fluid-tight seal between guide wire 22 and distal piston 7. The sealing means (e.g., O-ring) 25 is mounted in recess 26 and is held in place by a retaining ring 27.

FIG. 3 depicts the way in which piston 7 is rotated in a predetermined direction. In FIG. 3 the development of closed wave shaped groove 13 is shown. Dashed lines 1-1 and 2-2 represent the same spatial line. The wave-shaped groove 13 is longitudinally symmetrical and thus has no effect on the direction of rotation of distal piston 7. Sloped cutouts 30 and 31 determine the direction of rotation.

Proximal movement of distal piston 7 is equivalent to a rightward movement of closed wave-shaped groove 13 in FIG. 3. When cutouts 31 encounter stationary pins 14, upward movement of the distal piston results. This movement is equivalent to a counterclockwise (CCW) rotation of distal piston 7 (when viewed proximally). Distal movement of distal piston 7 also will result in the same CCW rotation due to similar reasoning but this time it will encounter cutouts 30 rather than cutouts 31. The direction of rotation is dependent on the slope direction of cutouts 30 and 31. The effect causes reciprocating movement of distal piston 7 in a continuous CCW rotation.

FIG. 4 shows the proximal end of the apparatus according to one embodiment of the present invention. The proximal end provides several functions:

a) Aspiration of blood and tissue debris from the cutting head 16.
(b) Creation of fluctuating or pulsatile pressure required for the movement of distal piston 7.
(c) Control movement of guide wire 22 and fixing its position when necessary.

As shown in FIG. 4, outer tube 1 and inner tube 2 are connected to support block 40 which may generally have a rectangular shape. As noted above, an annular passage 4 is defined between outer tube 1 and inner tube 2. Annular passage 4 serves for transferring blood and tissue debris from the distal end of the catheter to the proximal end thereof. As shown, passage 4 is opened to chamber 41.

A duct 42 connects chamber 41 and chamber 43. In operation, aspiration at the distal end of the catheter is performed when suction piston 44 moves upwards. Sealing means (e.g., O-ring) 45 maintains the vacuum in chamber 43. When a vacuum is created by the upward movement of suction piston 44, check valve 46 is opened and simultaneously check valve 47 is closed causing aspiration of blood and tissue debris from the distal end of the catheter into chamber 43.

After aspiration, suction piston 44 moves downward. As the suction piston moves downward check valve 46 is closed and check valve 47 is opened thus forcing out blood and tissue debris from chamber 43 into removable collecting bag 48 via tube 49. To maintain a vacuum, opening 42 and chamber 43 are closed with plate 50. Plate 50 contains sealing means (e.g., elastic gasket) 51 and is assembled to block 40 with screws 52.

Reciprocating drive unit 53 is fastened to plate 50 with screws 54. The drive unit 53 can be of any type that provides reciprocating motion e.g., linear actuator, crank mechanism, etc. Drive unit 53 is connected to suction piston 44 via rod 56, which passes through sealing means (e.g., O-ring) 57. Drive unit 53 is operated by switch 55.

A pressure piston 58 having a sealing means (e.g., O-ring) 59 is connected to rod 56, which is a part of drive unit 53. The reciprocating movement of drive unit 53 and the attached pressure piston 58 produces pressure fluctuations. These pressure fluctuations are transferred via opening 60, chamber 61, and inner tube 2 to distal piston 7. Fluid 28 can be added to inner tube 2 if desired via opening 62 and valve 63.

Block 40 contains another opening 64 through which guide wire 22 passes. A sealing means (e.g., O-ring) 65 is located in recess 66 and forms a fluid-tight seal between block 40 and guide wire 22. Pressure on sealing means 65 is maintained by threaded fitting 67. Guide wire 22 passes through opening 68 and through chucks 69 that are part of fixing nut 70. Tightening fixing nut 70 squeezes 16 chucks 69 against tapered recess 71 and against guide wire 22 thus preventing guide wire 22 from moving.

FIG. 5 depicts an alternate embodiment of the distal end of the catheter. The basic idea of this embodiment is similar to the one described in FIGS. 1–3. The difference between the two embodiments is the way in which tissue debris is removed from the occlusion site. In the embodiment of FIGS. 1–3, debris is aspirated via the catheter to the proximal end. In the embodiment shown in FIG. 5, debris is collected into a collecting 82 located next to the cutting head and removed from the collection chamber after the catheter is removed from the patient.

In FIG. 5 the catheter comprises a tube 80 which, if desired can be provided with a braided reinforcement 83. The distal part of tube 80 is located in housing 81. A distal piston 7 is housed within housing 81. Distal piston 7 is driven by fluid 28 which is applied through tube 80. A sealing means (e.g., O-ring) 11 at the distal end of distal piston 7 provides a fluid-tight seal between tube 80 and chamber 12. The pressure of fluid 28, which originates at the proximal end of the apparatus, fluctuates. The way the pressure fluctuates will be discussed below with reference to FIG. 6.

As the fluid pressure rises in tube 80 distal piston 7 is forced distally in a rotational movement. The rotation is effected by the presence of a closed wave-shaped groove 13 formed in the outer circumferential surface of distal piston 7. The movement of distal piston 7 is directed by one or more stationary pins 14 assembled in housing 81 which protrude into wave-shaped groove 13. The pattern of closed wave-shape groove 13 may vary according to the number of pins 14 and according to the desired ratio of reciprocating to rotational movement.

Following a reduction in the fluid pressure in tube 80, distal piston 7 is pushed proximally by spring means 15 and drawn by a vacuum created in tube 80. Simultaneously, piston 7 undergoes a rotational movement in the same way as previously described.

A cutting head 16 is located within housing 81. Cutting head 16 has a stem 17 that passes through a central hole 18 in housing 80 and is connected to distal piston 7. The distal section of cutting head 16 has one or more cutting blades 19. Blood and tissue debris are drained via opening 21 in cutting head 16 and stored in chamber 82. Cutting head 16 is connected to distal piston 7 and therefore follows the same rotational and reciprocating motion as distal piston 7. This combined movement facilitates an incision of the occlusion.

In FIG. 5 the cutting head 16 is shown at its most distal location. When no pressure is applied to distal piston 7, spring 15 forces cutting head 16 to move proximally so that it is concealed in housing 81. This manner of concealing the cutting head ensures that no injury will be caused during insertion of the catheter into a patient's vessel. The way in which piston 7 rotates in a predetermined direction is explained above in reference to FIG. 3.

As shown in FIG. 5, a guide wire 22 extends distally in front of cutting head 16 for guiding the catheter through a patient's vessel. Guide wire 22 passes through tube 80 all the way up to the proximal end. The distal end of guide wire 22 passes through hole 23 in distal piston 7 and through hole 24 in stem 17. Alternatively, guide wire 22 can be shorter and its proximal end can be connected to the inner circumference of housing 81. A sealing means is provided for forming a fluid-tight seal between guide wire 22 and distal piston 7. The sealing means (e.g., 0-ring) 25 is mounted in recess 26 and is held in place by a retaining ring 27.

FIG. 6 shows an alternative proximal end of the apparatus. The proximal end shown in FIG. 6 provides two functions:
(a) Creation of fluctuating pressure required for the movement of distal piston 7;
(b) Control movement of guide wire 22 and fixing its position when necessary.

As shown in FIG. 6, a syringe pump 91 is fixed to housing of drive unit 96 by bracket 95 and clamp 92. The syringe piston 90 is connected to rod 94 via bracket 93. Rod 94 is a part of drive unit 96 which moves in a reciprocating manner. The drive unit 96 can be of any type that provides reciprocating motion e.g., linear actuator, crank mechanism, etc. The speed and direction of this movement is controlled by drive unit 96. Drive unit 96 is operated by switch 97. The movement of syringe piston 96 produces fluctuating pressure in fluid 28. This pressure is transferred to the distal end of the catheter via tube 80.

As shown in FIG. 6, the proximal end of the catheter also contains a T-shaped or branched fitting 98. Guide wire 22 passes through one opening in fitting 98. A sealing means 65 is located in recess 66 and forms a fluid-tight seal between block support fitting 98 and guide wire 22. Pressure on sealing means 65 (e.g., O-ring) is maintained by fitting 67. Guide wire 22 passes through opening 68 and through chucks 69 that are part of fixing nut 70. Tightening fixing nut 70 squeezes chucks 69 against tapered recess 71 and against guide wire 22 thus preventing guide wire 22 from moving.

The materials from which the various elements of this catheter are constructed can be selected from known materials which are conventionally utilized in catheters. The braided reinforcement elements noted above likewise can be constructed from woven or laminated strands of known materials such as nylon.

While the present invention has been described as a catheter device, it is noted that the general structure of the device can be readily adapted for any type of drilling apparatus, including large scale drilling such as oil drilling and earth boring.

Although the present invention has been described with reference to particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims which follow.

What is claimed is:

1. A device for removal of intraluminal occlusions which comprising:
   a catheter having a distal end for insertion into a patient and a proximal end;
   a distal piston located within said distal end of said catheter for simultaneous longitudinal and rotational movement therein, said distal piston including a closed wave-shaped groove in a circumferential surface thereof which receives at least one stationary pin fixed to an inner portion of said distal end of said catheter; and
   a cutting head, said cutting head being attached to said distal piston for simultaneous longitudinal and rotational movement together with said distal piston.

2. A device for removal of intraluminal occlusions according to claim 1, wherein said cutting head is positioned within the distal end of the catheter so that at a one position of a path along its longitudinal motion said cutting head is within a distal end of said catheter and at another position along the path of its longitudinal motion said cutting head extends beyond the distal end of said catheter.

3. A device for removal of intraluminal occlusions according to claim 1, wherein said cutting head includes at least one cutting blade.

4. A device for removal of intraluminal occlusions according to claim 1, wherein said catheter includes a chamber between said distal piston and said cutting head for receiving material cut by said cutting head, and said cutting head includes at least one through bore through which the cut material can pass into said chamber.

5. A device for removal of intraluminal occlusions according to claim 4, wherein said chamber is connected to a passage which extends to said proximal end of said catheter.

6. A device for removal of intraluminal occlusions according to claim 1, wherein said catheter includes a guide wire which extends through said distal piston and said cutting head.

7. A device for removal of intraluminal occlusions according to claim 6, wherein said guide wire extends beyond said distal end of said catheter.

8. A device for removal of intraluminal occlusions according to claim 6, wherein said catheter includes a branched fitting near said proximal end thereof and said guide wire enters said catheter through said branched fitting.

9. A device for removal of intraluminal occlusions according to claim 8, wherein said branched fitting includes means to secure said guide wire.

10. A device for removal of intraluminal occlusions according to claim 1, wherein a pump means is provided at said proximal end of said catheter for applying fluid pressure to said distal piston for driving said distal piston.

11. A device for removal of intraluminal occlusions according to claim 10, wherein said pump means comprises a reciprocating pump means.

12. A device for removal of intraluminal occlusions according to claim 11, wherein said pump means comprises dual pumping means to apply fluid pressure to said distal piston for driving said distal piston and for applying a vacuum to aspirate material cut by said cutting head from said distal end of said catheter.

13. A device for removal of intraluminal occlusions according to claim 12, wherein said pump means includes a single piston which performs said dual pumping.

14. A device for removal of intraluminal occlusions according to claim 12, wherein said pump means includes a chamber for collecting material aspirated from said distal end of said catheter.

15. A device for removal of intraluminal occlusions according to claim 10, wherein said pump means is attached to a support block through which a guide wire passes.

16. A device for removal of intraluminal occlusions according to claim 15, wherein said support block includes means to secure said guide wire.

17. A method of removing intraluminal occlusions which comprises:
   providing a catheter having a distal end for insertion into a patient with a cutting head for simultaneous longitudinal and rotational movement;
   inserting said distal end of said catheter into a lumen of a patient while maintaining said cutting head within said distal end of said catheter;
   positioning said distal end of said catheter near an object to be removed and;
   causing said cutting head to simultaneously move in both a longitudinal and a rotational movement so as to extend from said distal end of said catheter and cut said object to be removed, said step of causing including the steps of applying a pulsatile driving force to said cutting head to cause said cutting reciprocate longitudinally, and rotating said cutting response to longitudinal reciprocation of the cutting head.

18. A method of removing intraluminal occlusions according to claim 17, further including the step of collecting material cut by said cutting head in a chamber provided in said distal end of said catheter behind said cutting head.

19. A method of removing intraluminal occlusions according to claim 17, further including the step of aspirating material cut by said cutting head and removing said aspirated material from a proximal end of said catheter.

20. The method of claim 17:
   wherein said step of applying a pulsatile driving force includes applying said force to a piston secured to said cutting head and disposed in a chamber of said device; and
   wherein said step of rotating comprises projecting a pin, positionally fixed relative to said chamber, radially into said chamber and into a closed wave-shaped groove defined circumferentially in said piston to guide said piston rotationally as the piston moves longitudinally.

21. A device for removal of intraluminal occlusions which comprising:
   a catheter having a distal end for insertion into a patient and a proximal end;
   a distal piston located within said distal end of said catheter for simultaneous longitudinal and rotational movement therein, said distal piston including at least one stationary pin fixed thereto which is received in a closed wave-shaped groove formed in an inner surface of said distal end of said catheter; and
   a cutting head attached to said distal piston for simultaneous longitudinal and rotational movement together with said distal piston.

22. A device for removal of intraluminal occlusions comprising:
   a catheter having a longitudinal axis and a distal end adapted for insertion into a passage in a patient's body;
   a driven member located within said catheter;
   means for simultaneously reciprocating said driven member longitudinally in said catheter and rotating said driven member about said longitudinal axis; and
   a device head secured to said driven member for reciprocation longitudinally and rotating therewith, said device head projecting from said distal end when reciprocating longitudinally and rotating to remove occluding material from said passage in the patient's body;
   wherein said means comprises:
   driving means for longitudinally reciprocating said driven member within said catheter; and
   further means responsive to longitudinal reciprocation of said driven member for rotating said driven member about said longitudinal axis.

23. The device of claim 22 wherein said further means comprises:
   a closed wave-shaped groove defined circumferentially in said driven member; and
   a stationary pin projecting radially into said groove to cause said piston, while longitudinally reciprocating, to rotate as said pin rides along said groove.

24. In a device for removing intraluminal occlusions, the method of simultaneously reciprocating a cutting head longitudinally and rotating the reciprocating cutting head, said method comprising the steps of:
   longitudinally reciprocating said cutting head by applying a pulsating force to said device; and
   in response to longitudinal reciprocation of said cutting head, directing said cutting head rotationally about its longitudinal axis.

* * * * *

UNITED STATES PATENT AND TRADEMARK OFFICE
CERTIFICATE OF CORRECTION

PATENT NO. : 5,350,390
DATED : September 27, 1994
INVENTOR(S) : Arieh Sher

It is certified that error appears in the above-identified patent and that said Letters Patent is hereby corrected as shown below:

The Drawing Sheet, consisting of Fig. 4, should be deleted to be replaced with the drawing sheet, consisting of Fig. 4, as shown on the attached page.

Column 7, line 43, after "collecting" add --chamber--.

In the Abstract, line 6, after "attached" change the comma to a period.

Signed and Sealed this

Twenty-ninth Day of November, 1994

*Attest:*

BRUCE LEHMAN

*Attesting Officer*          *Commissioner of Patents and Trademarks*